United States Patent [19]

Zarnack et al.

[11] Patent Number: 5,314,588
[45] Date of Patent: May 24, 1994

[54] PROCESS FOR RECOVERING POLYSOCYANATES FROM THE DISTILLATION RESIDUES OBTAINED IN THE PRODUCTION OF TOLYLENE DIISOCYANATE

[75] Inventors: Uwe J. Zarnack, Brunsbuettel; Volker Weintritt, Marne; Christian König, Kaarst, all of Fed. Rep. of Germany

[73] Assignee: Bayer Aktiengesellschaft, Leverkusen, Fed. Rep. of Germany

[21] Appl. No.: 928,561

[22] Filed: Aug. 11, 1992

[30] Foreign Application Priority Data

Aug. 20, 1991 [DE] Fed. Rep. of Germany ....... 4127514

[51] Int. Cl.$^5$ ............................................. B01D 3/10
[52] U.S. Cl. .................................. 203/38; 203/91; 203/DIG. 6; 203/DIG. 16; 521/160; 528/44; 560/352
[58] Field of Search ............... 203/38, 91, 29, DIG. 6, 203/DIG. 16; 521/160, 164; 528/44; 560/352

[56] References Cited

U.S. PATENT DOCUMENTS

| | | | |
|---|---|---|---|
| 3,128,310 | 4/1964 | Koch | 260/582 |
| 3,215,652 | 11/1965 | Kaplan | 521/160 |
| 3,331,876 | 7/1967 | Van Horn et al. | 260/582 |
| 3,426,058 | 2/1969 | Wagner et al. | 521/160 |
| 3,452,073 | 6/1969 | Shultz | 521/160 |
| 3,457,291 | 7/1969 | Baylor | 521/160 |
| 3,516,950 | 6/1970 | Haggis | 521/160 |
| 3,634,361 | 1/1972 | Shultz et al. | 260/77.5 AT |
| 3,755,215 | 8/1973 | Khoury et al. | 521/160 |
| 4,000,099 | 12/1976 | Nemoto et al. | 260/18 TN |
| 4,055,585 | 10/1977 | Okamoto et al. | 260/453 SP |
| 4,251,638 | 2/1981 | Reischl | 521/160 |
| 4,289,589 | 9/1981 | Koehler et al. | 203/49 |
| 4,304,708 | 12/1981 | Marx et al. | 260/37 R |
| 4,489,177 | 12/1984 | O'Connor et al. | 521/164 |

FOREIGN PATENT DOCUMENTS

| | | | |
|---|---|---|---|
| 0189156 | 7/1986 | European Pat. Off. | 521/160 |
| 269218 | 6/1988 | European Pat. Off. | |
| 2002064 | 7/1971 | Fed. Rep. of Germany | 521/160 |
| 2333150 | 1/1974 | Fed. Rep. of Germany | |
| 0848671 | 9/1960 | United Kingdom | 521/160 |
| 0874430 | 8/1961 | United Kingdom | 521/160 |
| 1346402 | 2/1974 | United Kingdom | |
| 1422056 | 1/1976 | United Kingdom | 521/160 |
| 1520055 | 8/1978 | United Kingdom | |

OTHER PUBLICATIONS

Database WPIL—AN 88-308139 & DD-A-257 827 (Veb Synthesewerk Schwarzheide) Abstract.

*Primary Examiner*—Virginia Manoharan
*Attorney, Agent, or Firm*—Joseph C. Gil; Godfried R. Akorli

[57] ABSTRACT

A process for recovering a distillate of tolylene diisocyanate and an isocyanate-group-containing sump product containing less than 200 ppm (by weight) tolylene diisocyanate from A) distillation residues obtained in the production of tolylene diisocyanate by mixing of the distillation residues A) with B) optionally urethane- and/or allophanate-modified polyisocyanates or polyisocyanate mixtures of the diphenyl methane series, heating of the mixture to 190° to 250° C. and simultaneously or subsequently working up by distillation.

3 Claims, 1 Drawing Sheet

PROCESS FOR RECOVERING POLYISOCYANATES FROM THE DISTILLATION RESIDUES OBTAINED IN THE PRODUCTION OF TOLYLENE DIISOCYANATE

BACKGROUND OF THE INVENTION

1. Field of Invention

This invention relates to a new process for recovering commercially useful polyisocyanates or polyisocyanate mixtures from the distillation residues obtained in the production of tolylene diisocyanate.

Considerable quantities of relatively high molecular weight secondary products of uretdione, isocyanurate, carbodiimide, uretoneimine, urea and biuret structures are unavoidably formed in the industrial production of tolylene diisocyanate (TDI) by phosgenation of tolylenediamine. These secondary products accumulate in the form of a tar-like, non-distillable residue during separation of the crude reaction mixture by distillation. This residue adversely affects the economy of industrial tolylene diisocyanate production and is unsuitable for the typical applications of polyisocyanates (production of polyurethanes).

2. Brief Description of the Prior Art

These industrially unavoidable TDI distillation residues have been partly recycled by alkaline hydrolysis. However, only a small percentage of tolylenediamines is recovered in the course of an extremely slow hydrolysis process (U.S. Pat No. 3,128,310 or 3,331,876).

DE-OS 2,915,830 describes a process for obtaining TDI by treatment of the distillation residue in a fluidized bed at 140° to 280° C.; the residue left after separation of the isocyanate accumulating is of a dust-like consistency. This process and also the processes according to DD-PS 130,143 or DE-OS 2,452,804 are confined solely to the recovery of the TDI remaining in the distillation residue. One disadvantage common to all the above-mentioned processes is the accumulation of an unusable residue.

U.S. Pat. No. 3,634,361, DE-OS 2,123,183, DE-OS 2,333,150, U.S. Pat. No. 3,634,361 and DE-OS 2,423,594 describe several processes in which TDI distillation residues still preferably containing more than 20% by weight free NCO groups are dissolved in an organic solvent in the presence of monomeric diisocyanates, optionally at high temperatures. On account of its high solvent content, the mixture is limited in its potential uses. In addition, these methods have been inhibited in practice by the inadequate storability and standardizability of the solutions and by the sedimentation of insoluble constituents in storage.

Methods of utilizing the TDI distillation residue as such are also known and include, for example, the use of the ground residue as a filler (DE-OS 2,850,609). Although this method enables the distillation residue to be fully utilized, it is attended by the major disadvantage that the valuable TDI present in the distillation residue cannot be recovered.

DD-PS 257,827 describes a process in which, after mixing with diphenyl methane diisocyanate or its higher homologs with the distillation residue obtained in the production of TDI, the mixture is subjected to a distillation process in which TDI is recovered as distillate and a bottom product is recovered as a further isocyanate component. In this process, the TDI is not completely recovered which is a major disadvantage from the toxicological and physiological point of view.

In addition, in the process according to this prior publication, either the distillation residue or the mixture to be distilled has to be pretreated with an acid acceptor or the bottom product accumulating has to be post-treated with an acid acceptor.

The problem addressed by the present invention is to provide a new process which would enable the TDI distillation residues obtained in the industrial production of TDI to be converted into a useful component containing isocyanate groups and the partly reversibly chemically bound TDI present in the distillation residue to be isolated as a further isocyanate component. In addition, the bottom distillation product accumulating would be stable in storage and further processable without any need for additives, for example acid acceptors, and the residual content of TDI in the bottom product would be below 200 ppm (by weight).

This problem has been solved by the process according to the invention which is described in detail in the following.

SUMMARY OF THE INVENTION

The present invention relates to a process for recovering a distillate consisting essentially of tolylene diisocyanate and an isocyanate-group-containing bottom product having a tolylene diisocyanate content of less than 200 ppm (by weight) from A) distillation residues from the production of tolylene diisocyanate by mixing of the distillation residues A) with B) optionally urethane- and/or allophanate-modified polyisocyanates or polyisocyanate mixtures of the diphenyl methane series having a NCO content of at least 15% by weight and working up of the mixture by distillation, characterized in that the mixture is heated to temperatures of 190° to 250° C. before or during working up by distillation so that the tolylene diisocyanate reversibly bound in the distillation residues A) is largely substituted by polyisocyanate B).

The distillation residues A) to be used in the process according to the invention are the distillation residues obtained in the reaction of tolylenediamine with phosgene in the presence of solvents and subsequent distillation of the reaction solution. In the context of the invention, "tolylenediamine" (TDA) is understood in particular to be 2,4-diaminotoluene and technical mixtures thereof with up to 35% by weight, based on the mixture, of 2,6-diaminotoluene. Accordingly, the term "tolylene diisocyanate" or "TDI" stands for 2,4-diisocyanatotoluene or technical mixtures thereof with up to 35% by weight, based on mixtures of 2,6-diisocyanatotoluene. The TDI distillation residues to be used in the process according to the invention are, in particular, the residues obtained in the production of technical 2,4-diisocyanatotoluene, technical mixtures of 80% 2,4- and 20% 2,6-diisocyanatotoluene or technical mixtures of 65% 2,4- and 35% 2,6-diisocyanatotoluene. In general, these technical distillation residues contain up to 85% by weight free and reversibly chemically bound, i.e. thermally removable, TDI.

The process according to the invention is based on the observation that not only the TDI dissolved in the distillation residue, but also the reversibly chemically bound TDI mentioned can be substituted by the polyisocyanate under the conditions of the process according to the invention.

DETAILED DESCRIPTION OF THE INVENTION

In the process according to the invention, the distillation residue A) is mixed with optionally urethane- and/or allophanate-modified polyisocyanates or polyisocyanate mixtures of the diphenyl methane series B).

The optionally urethane- and/or allophanate-modified polyisocyanates or polyisocyanate mixtures of the diphenyl methane series are those having an NCO content of at least 15% by weight and preferably of at least 25% by weight. Component B) consists either of 4,4'-diisocyanatodiphenyl methane or technical mixtures thereof with 2,4'- and, optionally, 2,2'-diisocyanatodiphenyl methane (mixtures such as these preferably containing at least 50% by weight and, more preferably, at least 70% by weight 4,4'-diisocyanatodiphenyl methane) or of mixtures of such diisocyanatodiphenyl methane isomers with their higher homologs containing more than two isocyanate groups per molecule, these mixtures generally containing up to 65% by weight higher homologs, or finally urethane- and/or allophanate-modified semi-prepolymers based on these polyisocyanates or polyisocyanate mixtures. These semi-prepolymers are modification products of the polyisocyanates or polyisocyanate mixtures with less than equivalent quantities of polyhydric alcohols or mixtures of (i) preformed NCO prepolymers or NCO semi-prepolymers based on polyisocyanates or polyisocyanate mixtures of the type mentioned and certain polyhydric alcohols with (ii) unmodified polyisocyanates or polyisocyanate mixtures of the diphenyl methane series. The semi-prepolymers usable in accordance with the invention are preferably semi-prepolymers of which at least 50% by weight consist of urethane-group-free polyisocyanates of the diphenyl methane series. Suitable polyhydric alcohols for the urethane and/or allophanate modification of the polyisocyanates or polyisocyanate mixtures whether in situ by addition of an alcohol to the polyisocyanate or polyisocyanate mixture or whether from partial urethanization or allophanatization of the polyisocyanates or polyisocyanate mixtures beforehand are, in particular, polyhydric alcohols containing ether groups and having a molecular weight in the range from 106 to 8,000 and preferably in the range from 200 to 2,000 which may be obtained in known manner by alkoxylation of suitable polyhydric starter molecules using ethylene oxide and/or propylene oxide. Examples are diethylene glycol, dipropylene glycol, tripropylene glycol or polyether polyols based on propylene glycol, glycerol and/or trimethylol propane which have been produced by propoxylation of these starters and, optionally, subsequent ethoxylation of the propoxylation products.

However, it is particularly preferred to use polyisocyanates or polyisocyanate mixtures of the diphenyl methane series free from urethane and allophanate groups of the type mentioned above as component B).

In the practical application of the process according to the invention, component B) is used in a quantity of 35 to 950 parts by weight and preferably in a quantity of 80 to 400 parts by weight per 100 parts by weight TDI distillation residue.

To carry out the process according to the invention, the mixtures are heated to temperatures of 190° to 250° C. and preferably to temperatures of 200° to 230° C. and are worked up by distillation either during and/or after the heat treatment.

Working up by distillation is preferably carried out at the same time as the heat treatment using a continuous reactor linked to a distillation column. The process according to the invention, which is preferably carried out in a single stage in such reactors, is preferably carried out under a pressure of 2 to 100 mbar preferably under a pressure of 5 to 40 mbar.

BRIEF DESCRIPTION OF THE DRAWINGS

The apparatus shown in FIG. 1 of the accompanying drawing is particularly suitable for carrying out the process according to the invention.

Figure 1:
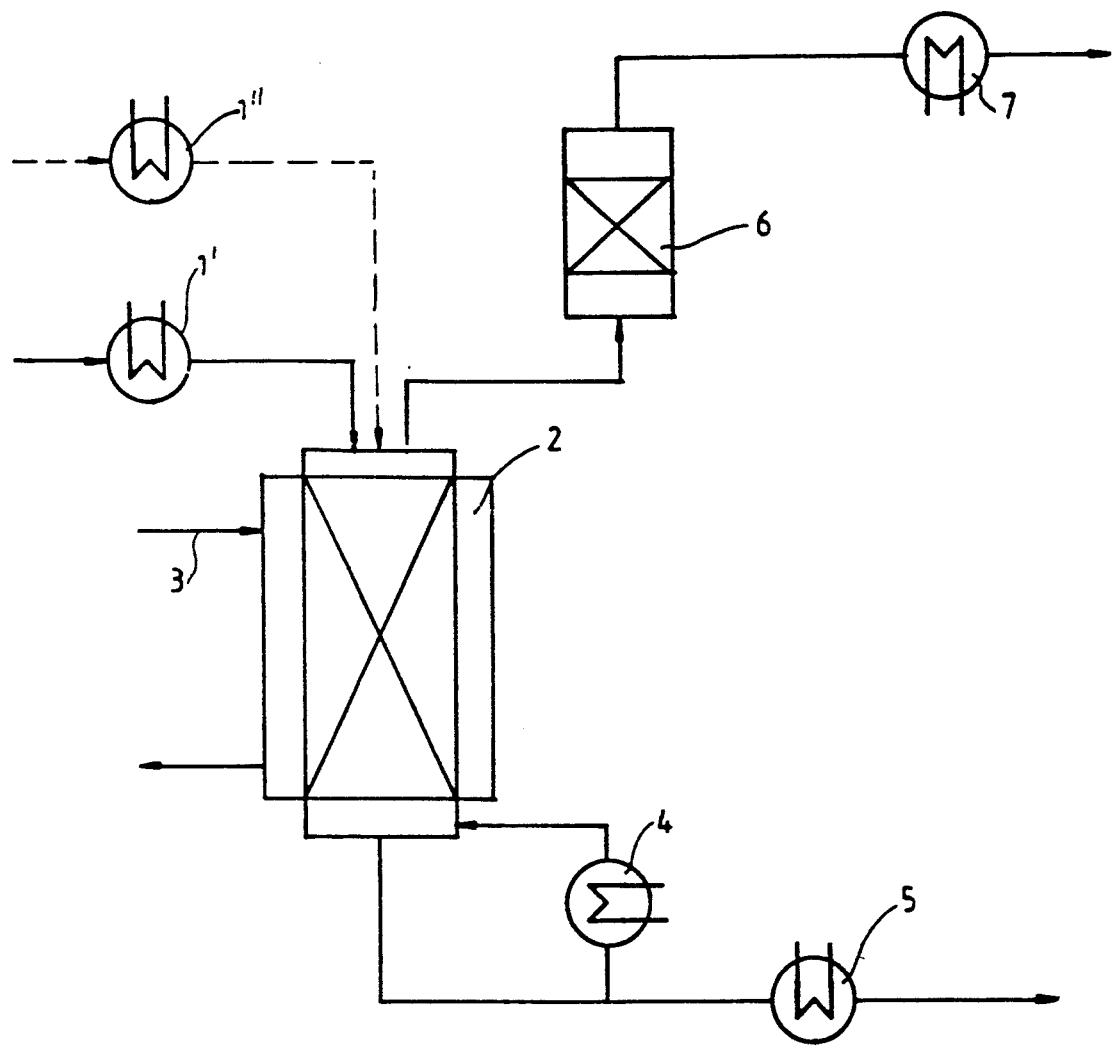
In FIG. 1 which is described as follows.

1') and 1")=a preheater;
2)=the reactor;
3)=the heat-exchange medium;
4)=a heat exchanger;
5)=a quench cooler;
6)=a distillation column and
7)=a condenser.

Reactors (2) in which fittings and/or structural packs similar to bubble trays of the type typically used in the field of distillation are installed to increase the residence time are particularly preferred. The distillation column (6) is preferably operated under such temperature and pressure conditions that only TDI with a purity of at least 99.5% accumulates as overhead product in the condenser (7) while virtually the entire quantity of component B) used is removed via the sump. On the other hand, the temperature and pressure conditions in the reactor (2) and in the distillation column (6) are selected within the ranges mentioned so that the TDI released or substituted by polyisocyanates B) is almost exclusively obtained as distillate and the TDI content in the bottom product is at most 200 ppm and preferably at most 125 ppm (by weight).

It has been found to be of advantage to gauge the quantities of starting components A) and B) used within the ranges mentioned so that the content of distillation residue components in the bottom product removed via the condenser (5) is at most 30% by weight.

The starting components A) and B) may be mixed before the reactor (2) and introduced into the reactor in the form of a mixture, optionally via one of the preheaters (1') and (1"), or separately, preferably through the preheater mentioned, so that the mixture of A) and B) is only formed in the reactor itself. In general, the starting component A) and B) or the mixture prepared therefrom beforehand are/is preheated in the preheater or in the preheaters at temperatures of at least 70° C., the mixture being further heated in the reactor.

In one preferred embodiment of the process according to the invention, the sump product accumulating with a temperature of at least 190° C. is cooled for at most 1 minute to below 80° C. and preferably to below 60° C., for example by passage through the quench cooler (5). In this way, the resulting solution remains stable in storage and in viscosity without any need for further additives.

The mixture containing isocyanate groups which is obtained as the bottom product generally has a viscosity at 25° C. of 200 to 10,000 mPa.s and an NCO content of 23 to 31% by weight. By virtue of its low TDI content, it is a valuable starting material for the production of polyurethane plastics in the processing of which TDI emissions are far below the maximum allowable concentration, even at high processing temperatures. The subsequent emission of TDI can be ruled out, even at relatively high processing and in-use temperatures.

The TDI obtained as distillate may be used for all TDI applications. If desired, it may be subjected to further working up by distillation together with crude fresh TDI.

The process according to the invention is illustrated by the following non-limiting Examples.

EXAMPLES

A mixture of 4,424 g/h TDI distillation residue and 5,397 g/h diisocyanatodiphenyl methane heated to 90° C. in the preheater (1') is fed continuously into the reactor (2)—operated at 200° C./8 mbar—of a continuous laboratory plant as illustrated in the drawing. The TDI distillation residue is a distillation residue containing a total of 66.3% by weight dissolved and thermally removable TDI which was obtained in the working up by distillation of the phosgenation product of tolylenediamine (80% by weight 2,4- and 20% by weight 2,6-isomer) in dichlorobenzene. The diisocyanatodiphenyl methane was an isomer mixture of 93.8% by weight 4,4'-, 5.9% by weight 2,4'- and 0.3% by weight 2,2'-diisocyanatodiphenyl methane.

The bottom product leaving the reactor in a quantity of 6,823 g/h and with a temperature of 200° C. is quenched to 50° C. in the quench cooler (5) (average residence time in the quench cooler: 30 seconds). The non-sedimenting, viscosity-stable product thus obtained has a viscosity at 25° C. of 326 mPa.s, a TDI content of 60 ppm (by weight) and an NCO content of 28% by weight. It may readily be used as polyisocyanate component in the production of polyurethane plastics by the isocyanate polyaddition process.

The TDI obtained at the head of the column (6) in a quantity of 22,933 g/h (head temperature of the column 115° C.) has a residual content of 0.04% by weight diisocyanatodiphenyl methane. It may be used for typical TDI applications, for example for the production of flexible polyurethane foams.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for recovering a distillate consisting essentially of tolylene diisocyanate and isocyanate-group-containing bottom product having a tolylene diisocyanate content of less than 200 ppm (by weight) from A) a distillation residue from the production of tolylene diisocyanate by mixing of the distillation residue A) with B) a urethane-and/or allophonate-modified polyisocyanate or polyisocyanate mixture of diphenyl methane series having an NCO content of at least 15% by weight, and working up of the mixture by distillation comprising heating the mixture to temperatures of 190° to 250° C. before or during working up by distillation so that reversibly bound tolylene diisocyanate in the distillation residue A) is largely substituted by polyisocyanate B); the process is carried out in a single stage in a continuous reactor (2) linked to a distillation column under a pressure kept at 2 to 100 mbar.

2. A process as claimed in claim 1, wherein the starting components A) and B) are separately introduced into the reactor (2) via preheaters (1') and (1"), 3. A process for recovering a distillate consisting essentially of tolylene diisocyanate and isocyanate-group-containing bottom product having a tolylene diisocyanate content of less than 200 ppm (by weight) from A) a distillation residue from the production of tolylene diisocyanate by mixing of the distillation residue A) with B) a urethane-and/or allophonate-modified polyisocyanate or polyisocyanate mixture of diphenyl methane series having an NCO content of at least 15% by weight, and working up of the mixture by distillation comprising heating the mixture to temperatures of 190° to 250° C. before or during working up by distillation so that reversibly bound tolylene diisocyanate in the distillation residue A) is largely substituted by polyisocyanate B); the bottom product which accumulates with a temperature of at least 190° C. is quenched to a temperature below 80° C. in at most 1 minute.

* * * * *